(12) United States Patent
Fung et al.

(10) Patent No.: US 11,333,604 B2
(45) Date of Patent: *May 17, 2022

(54) DETECTOR WITH REDUCED FLUORESCENCE RANGE NOISE

(71) Applicant: Illumina, Inc., San Diego, CA (US)

(72) Inventors: Tracy H. Fung, San Mateo, CA (US); Poorya Sabounchi, Atherton, CA (US); Bernard Hirschbein, San Francisco, CA (US); Joseph Pinto, Solana Beach, CA (US); Tarun Khurana, Fremont, CA (US); Randall Smith, San Marcos, CA (US); Wenyi Feng, San Diego, CA (US)

(73) Assignee: ILLUMINA, INC., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/948,524

(22) Filed: Sep. 22, 2020

(65) Prior Publication Data
US 2021/0003505 A1   Jan. 7, 2021

Related U.S. Application Data

(63) Continuation of application No. 16/778,935, filed on Jan. 31, 2020, now Pat. No. 10,883,937, which is a
(Continued)

(51) Int. Cl.
*G01N 21/64*   (2006.01)
*G01N 33/53*   (2006.01)

(52) U.S. Cl.
CPC ..... *G01N 21/6428* (2013.01); *G01N 21/6454* (2013.01); *G01N 33/53* (2013.01); *G01N 2021/6471* (2013.01); *G01N 2201/08* (2013.01)

(58) Field of Classification Search
None
See application file for complete search history.

(56) References Cited

U.S. PATENT DOCUMENTS 6,506,506 B1   1/2003   Tomiuchi et al.
8,906,320 B1   12/2014  Eltoukhy et al.
(Continued)

FOREIGN PATENT DOCUMENTS

CN   102361940   2/2012
CN   102906239   1/2013
(Continued)

OTHER PUBLICATIONS

Abramowitz, M., et al., "Fluorescence Microscopy, Transmitted Light Illumination", https://micro.magnet.fsu.edu/primer/techniques/fluorescence/anatomy/translightpaths.html, 1998.
(Continued)

*Primary Examiner* — Edwin C Gunberg
(74) *Attorney, Agent, or Firm* — Illumina, Inc.

(57) ABSTRACT

There is set forth herein a device comprising structure defining a detector surface configured for supporting biological or chemical substances, and a sensor array comprising light sensors and circuitry to transmit data signals using photons detected by the light sensors. The device can include one or more features for reducing fluorescence range noise in a detection band of the sensor array.

19 Claims, 7 Drawing Sheets

Related U.S. Application Data continuation of application No. 16/206,564, filed on Nov. 30, 2018, now Pat. No. 10,551,317.

(60) Provisional application No. 62/644,804, filed on Mar. 19, 2018, provisional application No. 62/611,464, filed on Dec. 28, 2017.

(56) References Cited

U.S. PATENT DOCUMENTS

| | | | |
|---|---|---|---|
| 10,254,225 B2 | 4/2019 | Zhong et al. | |
| 10,551,317 B2* | 2/2020 | Fung | G02B 5/223 |
| 10,883,917 B2* | 1/2021 | Wu | G01N 21/51 |
| 2004/0179283 A1 | 9/2004 | Jones et al. | |
| 2004/0241458 A1 | 12/2004 | D'Haene et al. | |
| 2007/0002325 A1 | 1/2007 | Tabata et al. | |
| 2007/0145498 A1 | 6/2007 | Metx et al. | |
| 2008/0039339 A1 | 2/2008 | Hassibi et al. | |
| 2008/0081769 A1 | 4/2008 | Hassibi | |
| 2009/0111207 A1 | 4/2009 | Choumane et al. | |
| 2009/0189058 A1 | 7/2009 | Mitsui et al. | |
| 2010/0065726 A1 | 3/2010 | Zhong et al. | |
| 2010/0204064 A1* | 8/2010 | Cho | G01N 21/6454 506/17 |
| 2012/0014837 A1 | 1/2012 | Fehr et al. | |
| 2012/0019828 A1 | 1/2012 | McCaffrey et al. | |
| 2012/0021525 A1 | 1/2012 | Fehr et al. | |
| 2014/0248693 A1 | 9/2014 | Maher | |
| 2014/0263948 A1 | 9/2014 | Lee et al. | |
| 2015/0079596 A1 | 3/2015 | Eltoukhy et al. | |
| 2015/0116484 A1 | 4/2015 | Kim et al. | |
| 2016/0061740 A1 | 3/2016 | Grot et al. | |
| 2016/0356715 A1 | 12/2016 | Zhong et al. | |
| 2017/0016830 A1 | 1/2017 | Chung et al. | |
| 2017/0102530 A1 | 4/2017 | Chang et al. | |
| 2017/0107562 A1 | 4/2017 | Rothberg et al. | |
| 2019/0060897 A1* | 2/2019 | Makino | G01N 21/6458 |
| 2020/0083297 A1 | 3/2020 | Masahiro et al. | |

FOREIGN PATENT DOCUMENTS

| | | |
|---|---|---|
| EP | 2221606 | 8/2010 |
| JP | 2001091726 | 4/2001 |
| JP | 2002022935 | 1/2002 |
| JP | 2009540299 | 11/2009 |
| JP | 2017504789 | 2/2017 |
| KR | 20140112866 | 9/2004 |
| KR | 20130109668 | 10/2013 |
| RU | 133932 | 10/2013 |
| TW | 201713932 | 4/2017 |

OTHER PUBLICATIONS

Coskun, A., et al., "Lensfree On-Chip Fluorescence Microscopy for High-Throughput Imaging of Bio-Chips", Sensors: Proceedings of the First National Conference on Sensors, Lecture Notes in Electrical Engineering 162, Feb. 15-17, 2012.

Greenbaum, A., et al., "Imaging without lenses: achievements and remaining challenges of wide-field on-chip microscopy", Nat Methods, 9(9), 889-895, Sep. 2012.

\* cited by examiner

DETECTOR WITH REDUCED FLUORESCENCE RANGE NOISE

CROSS-REFERENCE TO RELATED APPLICATIONS

This application is a continuation of U.S. application Ser. No. 16/778,935, filed Jan. 31, 2020, entitled "Detector With Reduced Fluorescence Range Noise," which is a continuation of U.S. application Ser. No. 16/206,564, filed Nov. 30, 2018, now U.S. Pat. No. 10,551,317, issued Feb. 4, 2020, entitled "Detector With Reduced Fluorescence Range Noise," which claims priority to U.S. Patent Application No. 62/611,464, filed Dec. 28, 2017, entitled "Detector With Reduced Fluorescence Range Noise" and U.S. Patent Application No. 62/644,804, filed Mar. 19, 2018, entitled "Detector With Reduced Fluorescence Range Noise." The entire contents of each of the aforementioned applications are incorporated herein by reference.

BACKGROUND

Various protocols in biological or chemical research involve performing controlled reactions. The designated reactions can then be observed or detected and subsequent analysis can help identify or reveal properties of chemicals involved in the reaction.

In some multiplex assays, an unknown analyte having an identifiable label (e.g. fluorescent label) can be exposed to thousands of known probes under controlled conditions. Each known probe can be deposited into a corresponding well of a microplate. Observing any chemical reactions that occur between the known probes and the unknown analyte within the wells can help identify or reveal properties of the analyte. Other examples of such protocols include known DNA sequencing processes, such as sequencing-by-synthesis (SBS) or cyclic-array sequencing.

In some fluorescent-detection protocols, an optical system is used to direct excitation light onto fluorophores, e.g. fluorescently-labeled analytes and to also detect the fluorescent emissions signal light that can emit from the analytes having attached fluorophores. However, such optical systems can be relatively expensive and require a larger benchtop footprint. For example, the optical system can include an arrangement of lenses, filters, and light sources.

In other proposed detection systems, the controlled reactions in a flow cell define by a solid-state light sensor array (e.g. a complementary metal oxide semiconductor (CMOS) detector or a charge coupled device (CCD) detector). These systems do not involve a large optical assembly to detect the fluorescent emissions.

BRIEF DESCRIPTION

There is set forth herein a device comprising: structure defining a detector surface configured for supporting biological or chemical substances, and a sensor array comprising light sensors and circuitry to transmit data signals using photons detected by the light sensors. The device can include one or more feature for reducing fluorescence range noise in a detection band of the sensor array.

There is set forth herein a device comprising: a structure defining a detector surface configured for supporting biological or chemical samples; and a sensor array comprising light sensors and circuitry to transmit signals using photons detected by the light sensors; a guide array comprising light guides; wherein light guides of the guide array receive excitation light and emissions signal light from the detector surface, wherein the light guides extend toward respective light sensors of the sensor array and comprise filter material that blocks the excitation light and permits the emissions signal light to propagate toward the respective light sensors, and wherein the filter material comprises a metal complex dye.

There is set forth herein a method comprising: fabricating circuitry to transmit data signals using photons detected by a light sensor array; depositing filter material within guide cavities of a guide cavity array that are aligned with and disposed above respective light sensors of the light sensor array, wherein the filter material comprises dye suspended in a polymer matrix, the dye comprising a photon emission quencher; and fabricating a structure defining a detector surface for supporting biological or chemical samples, wherein the fabricating the structure defining the detector surface includes fabricating the structure defining the detector surface above cavities of the guide cavity array and light sensors of the light sensor array.

There is set forth herein a device comprising: a structure defining a detector surface for supporting biological or chemical samples; a sensor array comprising light sensors, and circuitry to transmit data signals based on photons detected by the light sensors; and a guide array comprising light guides; wherein light guides of the guide array receive excitation light and emissions signal light from the detector surface, wherein the light guides extend toward respective light sensors of the sensor array and comprise filter material that blocks the excitation light and permits the emissions signal light to propagate toward the respective light sensors, wherein the detector surface includes a reaction recess, the reaction recess comprising an index of refraction and a dimension sufficient to cancel background light energy incident on the detector surface in a detection band of the sensor array.

DRAWINGS

These and other features, aspects, and advantages of the present subject matter will become better understood when the following detailed description is read with reference to the accompanying drawings in which like characters represent like parts throughout the drawings, wherein.

DETAILED DESCRIPTION

Figure 1:
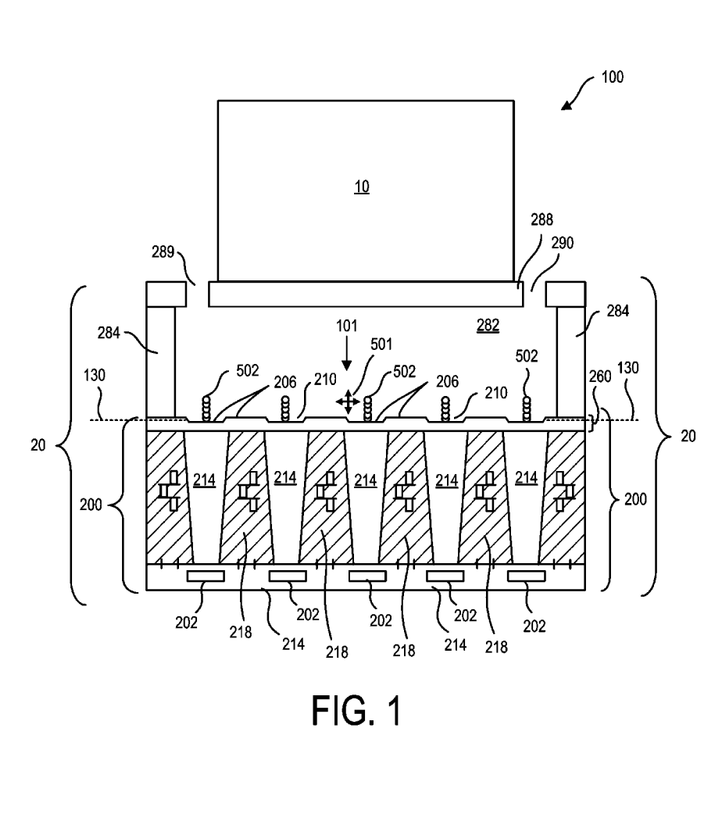
FIG. 1 is a schematic cutaway side view of a system for use in biological or chemical analysis having a detector that includes a detector surface for supporting a biological or chemical sample according to one example.

In FIG. 1 there is shown a system 100 for use in analysis, such as biological or chemical analysis. System 100 can include light energy exciter 10 and a detector assembly 20. Detector assembly 20 can include detector 200 and a flow cell 282. Detector 200 can include a plurality of light sensors 202 and detector surface 206 for supporting samples 502 such as biological or chemical samples subject to test. Detector 200 can also include a plurality of light guides that guide light from detector surface 206 to light sensors 202. Detector surface 206, sidewalls 284, and flow cover 288 can define and delimit flow cell 282. Detector surface 206 can have an associated detector surface plane 130.

In a further aspect, detector surface 206 can be recessed to include reaction recesses 210 (nanowells). According to one example, each light sensor 202 can be aligned to one light guide 214 and one reaction recess 210. Each reaction recess 210 can define therein one or more reaction sites and samples 502 can be supported on such reaction sites according to one example.

In another aspect, detector 200 can include dielectric stack areas 218, intermediate of the light guides 214. Dielectric stack areas 218 can have formed therein circuitry, e.g. for read out of signals from light sensors 202 digitization storage and processing.

According to one example, detector 200 can be provided by a solid-state integrated circuit detector, such as complementary metal oxide semiconductor (CMOS) integrated circuit detector or a charge coupled device (CCD) integrated circuit detector.

According to one example, system 100 can be used for performance of biological or chemical testing with use of fluorophores. For example, a fluid having one or more fluorophores can be caused to flow into and out of flow cell 282 through inlet port using inlet port 289 and outlet port 290. Fluorophores can attract to various samples 502 and thus, by their detection fluorophores can act as markers for the samples 502 e.g. biological or chemical analytes to which they attract.

To detect the presence of a fluorophore within flow cell 282, light energy exciter 10 can be energized so that excitation light 101 in an excitation wavelength range is emitted by light energy exciter 10. On receipt of excitation light 101 fluorophores attached to samples 502 radiate emissions signal light 501, which is the signal of interest for detection by light sensors 202. Emissions signal light 501 owing to fluorescence of a fluorophore attached to a sample 502 will have a wavelength range red shifted relative to a wavelength range of excitation light 101.

Light energy exciter 10 can include at least one light source and at least one optical components to illuminate samples 502. Examples of light sources can include e.g. lasers, arc lamps, LEDs, or laser diodes. The optical components can be, for example, reflectors, dichroics, beam splitters, collimators, lenses, filters, wedges, prisms, mirrors, detectors, and the like. In examples that use an illumination system, the light energy exciter 10 can be configured to direct excitation light 101 to reaction sites. As one example, fluorophores can be excited by light in the green wavelength range, e.g. can be excited using excitation light 101 having a center (peak) wavelength of about 523 nm.

Examples herein recognize that a signal to noise ratio of system 100 can be expressed as set forth in the equation of (1) hereinbelow.

$$SNR = \frac{\text{Signal}}{\sqrt{\text{Signal} + \text{Excitation} + AF + \text{Background} + \text{Dark Current} + \text{Read Noise}^2}} \quad (1)$$

where "Signal" is the emissions signal light 501, i.e. the signal of interest light attributable to the fluorescence of a fluorophore attached to a sample, "Excitation" is unwanted excitation light reaching the light sensors 202, "AF" is the autofluorescence noise radiation of one or more autofluorescence sources within detector 200, "Background" is unwanted light energy transmitted into detector 200 from a source external to detector 200, "Dark Current" is current flow is noise associated to random electron-hole pair generation in the absence of light and "Read Noise" is noise associated to analog-to-digital electronics.

Figure 2:
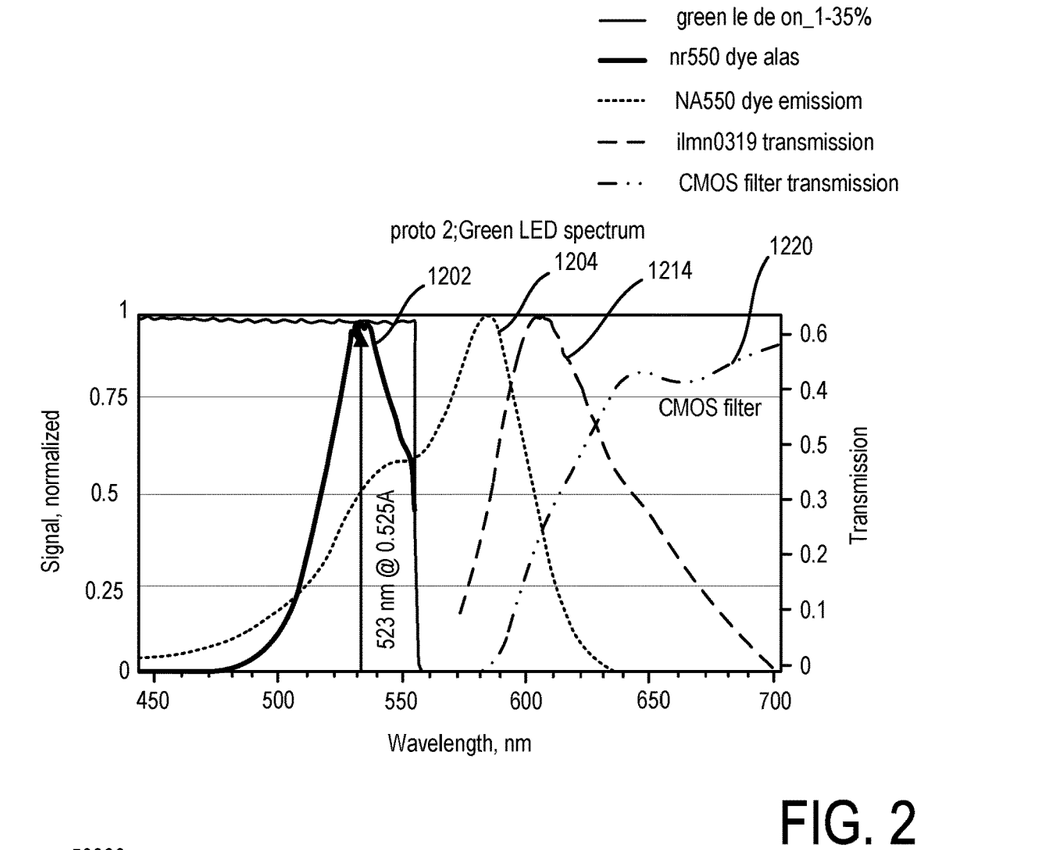
FIG. 2 spectral profile coordination diagram illustrating coordination between excitation wavelengths, absorption wavelengths, fluorescence emissions signal wavelengths, and detection band wavelengths according to one example.

FIG. 2 is a spectral profile coordination diagram illustrating targeted coordination between a wavelength range of excitation light, a wavelength range of signal light and a detection wavelength range. In the spectral profile coordination diagram of FIG. 2 spectral profile 1202 is the spectral profile of excitation light 101 as emitted by light energy exciter 10. Spectral profile 1204 is the spectrum of absorption of a fluorophore being detected with use of excitation light 101 having a spectral profile 1202 and spectral profile 1214 is the spectral profile of the emissions signal light 501 caused by the fluorescence of a fluorophore on being excited by excitation light 101. Spectral profile 1220 is the transmission profile (detection band) of detector 200 and light sensors 202 according to one example. Detector 200 can be configured to detect light in the wavelength range indicated by spectral profile 1220. Thus, referring to the spectral profile coordination diagram of FIG. 2, detector 200 is able to detect emissions signal light 501 in the range of wavelengths wherein the spectral profile 1214 of the emissions signal light 501 and the detection band spectral profile 1220 of detector 200 and light sensors 202 intersect.

Detector 200 can include one or more filters that block excitation light 101 so that detector 200 having light sensors 202 does not detect excitation light 101. In one aspect, light guides 214 that guide light from detector surface 206 can comprise filter material so that light guides 214 block light in the wavelength range of excitation light 101. Light sensors 202 accordingly can receive emissions signal light 501 radiating from an excited fluorophore but not excitation light 101.

Examples herein recognize that light guides 214 designed to improve a signal to noise ratio of detector 200 can act as a source of noise within detector 200. Referring to the spectral profile diagram of FIG. 3 spectral profile 1304 is a spectral profile of a filter material having a dye that is without (absent) a photon emission quencher commonly used in optical systems under test by excitation illumination in an expected wavelength range of excitation light 101 of system 100. In the specific spectral profile diagram of FIG. 3, spectral profile 1304 illustrates a spectral profile of a filter material under illumination by green excitation light, e.g. according to the excitation light spectral profile 1202 depicted in the spectral profile coordination diagram of FIG. 2, having a center (peak) wavelength of about 523 nm.

Figure 3:
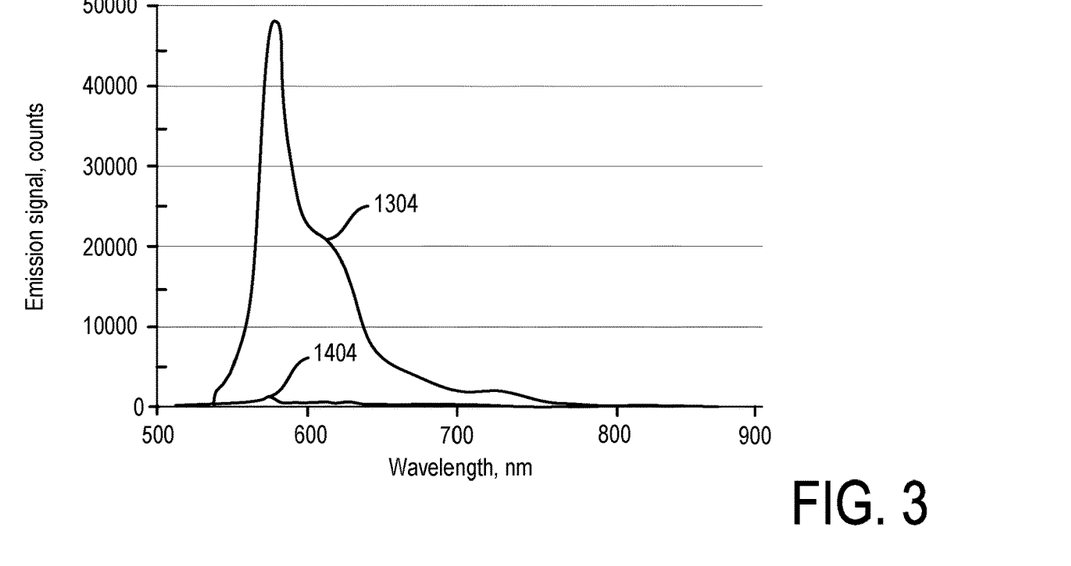
FIG. 3 is spectral profile diagram illustrating autofluorescence characteristics of filter materials according to one example.

Referring to the spectral profile diagram of FIG. 3 it is seen that the filter material having spectral profile characteristics depicted by spectral profile 1304 red shifts with respect to the emission band of excitation light 101 depicted by spectral profile 1202 of the spectral profile coordination diagram of FIG. 2, meaning that the material exhibits autofluorescence. Examples herein recognize that with filter material of light guides 214 autofluorescing, signal detected by light sensors 200 as an emissions signal can actually be noise radiation attributable to excitation light 101 operating to excite autofluorescence of light guides 214.

Examples to address unwanted autofluorescence of light guides 214 are described with reference to FIGS. 3-7. Referring to the energy state transition diagrams of FIGS. 4-6, light guides 214 according to one example can comprise material having a photon emission quencher. In another aspect, a filter material can include dye molecules to provide absorption in a wavelength band of excitation light 101.

Figure 4:
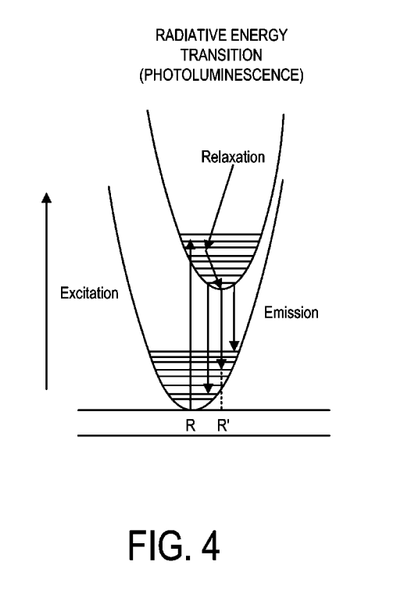
FIG. 4 is an energy state transition diagram illustrating energy state transitions of a radiant dye according to one example.
Figure 5:
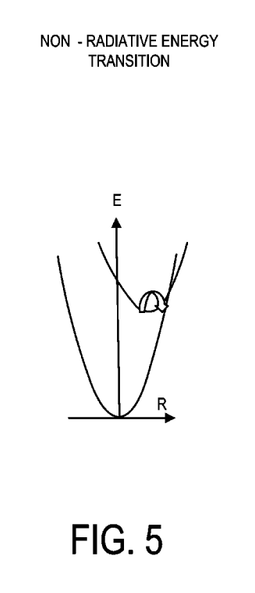
FIG. 5 is an energy state transition diagram illustrating energy state transitions of a dye having a photon emission quencher according to one example.

The energy state transition diagram of FIG. 4 depicts energy state transition of a dye without a photon emission quencher. On excitation and after an excitation state relaxation period the dye having the energy state transition characteristics as depicted in the energy state transition diagram of FIG. 4 emits photons on return to a ground state. FIG. 5 is an energy state transition diagram depicting energy state transitions of a dye having a photon emission quencher. Referring to the energy state transition diagram of FIG. 5, the dye having a photon emission quencher on excitation returns to a ground state after an excitation state relaxation period. However, by operation of the photon emission quencher, photons are not released on return to the ground state. Rather phonons are emitted on return to the ground state. The return to ground state is accompanied by the release of thermal energy rather than photons.

Dyes having the energy state transition characteristics as shown in the energy state transition diagram of FIG. 4 are radiant dyes and dyes having energy state transition characteristics as shown in the energy state transition diagram of FIG. 5 are non-radiant dyes.

A chemical structure diagram of a dye, according to one example, having a suitable photon emission quencher that quenches photon emissions is shown in (2).

(2)

The chemical structural diagram of (2) illustrates structural characteristics of a metal complex dye that functions as a photon emission quencher to quench photon emissions. According to one example, a metal complex dye can be provided by an octahedral transition metal complex dye as shown in (2). The specific metal complex dye shown in (2) includes two dye molecules+chromium ion, and some complexes can include one dye molecule+one chromium (Cr) ion or other metal ion. The structure depicted in (2) includes six ligand bonds: O, N and a standard crystal field. According to the structure depicted in (2), there is a photon emission quencher provided by a trivalent Cr transition metal ion. According to one example $Cr^{3+}$ can provide photon emission quenching functionality. Other transition metals can be used. Transition metals for use in a metal complex dye herein can include e.g. Scandium, Titanium, Vanadium, Chromium, Manganese, Iron, Cobalt, Nickel, Copper. For selection of alternative metals, energy levels can be overlapping between the metal ion and a dye molecule. According to one example, a transition metal for use in a metal complex dye can be selected to have an absorption spectral profile overlapping a fluorescence emissions profile of the selected dye so that the transition metal can provide photon emission quenching functionality through the fluorescence emission spectral profile of the selected dye.

In the example of the metal complex dye depicted in the structural diagram of (2), the metal complex dye has an associated proton depicted. The counter ion associated to the metal complex dye is formed by absorbing the positive (+) charge specified by the proton of the metal complex dye depicted in the structural diagram of (2) and can be selected according to one example for hydrophobicity performance and UV absorption performance. In one example, an alkyl amine, a primary amine, a secondary amine, or a tertiary amine may associate with the metal complex dye forming a counter ion, which can include an alkylammonium when associated with the metal complex dye.

The metal complex dye according to one example may not be particularly soluble in a solution on its own, and so the counter ion can be chosen to increase solubility. The counter ion can be selected for hydrophobicity performance in order to promote transparency and visibility of the polymer and/or solvent, and for reducing scattering. For instance, the counter ion can allow for the metal complex dye to be more evenly distributed, enhancing the visibility and transparency, and reducing scattering. The counter ion can be selected for UV absorption performance e.g. so that the counter ion does not undesirably contribute to fluorescence. For instance, absorption of the counter ion can affect the fluorescence characteristics by interfering with the spectrum of the metal dye complex, and can be chosen so as not to have an interfering spectrum. According to one example, a hydrophobic amine can be used as a counter ion. According to another example, it will be understood that depending on the metal center and the ligands chosen, a metal complex dye may have no charge, a net positive charge, or may have a net negative charge as well.

According to one example a counter ion associated to the metal complex dye depicted in the structural diagram of (2) can be provided by an alkyl amine. According to one example a counter ion associated to the metal complex dye depicted in the structural diagram of (2) can be provided by a tertiary amine. In a tertiary amine, a nitrogen has three organic substituents. According to one example, a counter ion associated to the metal complex dye depicted in the structural diagram of (2) can be provided by a tertiary alkyl amine.

Additionally, in other examples of a metal complex dye, a counter ion of appropriate charge can be selected to be associated to the metal complex dye. In some embodiments, a negatively or positively charged ion can be selected to counteract the net charge of the metal complex dye molecule, and/or adding to the hydrophobicity in some embodiments to allow for the metal complex dye to be incorporated into a solution. Additionally, when there is no charge, no counter ion may be necessary in some embodiments. The counter ion may include any charged particles, and in some embodiments includes primary, secondary, or tertiary amines. In further embodiments, a quaternary ammonium ion can be selected.

According to one example, the counter ion associated to the metal complex dye as depicted in (2) can include an amine, for instance an NR'R"R'", where at least one of the R groups is a chain, straight or branched, with at least four atoms. In some embodiments, there can be at least 10 atoms in the chain. The chain can include a long chain, and can include a polymer. The chain may be a mostly hydrocarbon group, or could include other moieties, such that the dye can possibly be soluble in any solvent necessary, and the polymer can be soluble in a solvent depending on the functional groups of the polymer. The other R groups can be the same or hydrogen, or can comprise a different chain. The chain can be according to one example a C4 to C20, including cyclic, chains or rings. In some embodiments, the counter ion can include more than one type of counter ion. Examples herein recognize that some mixtures of counter ions are convenient for use in solutions where more than one polymer material can be used. That is, some alkyl groups can be different, and the counter ion can include a plurality of counter ions.

Figure 6:
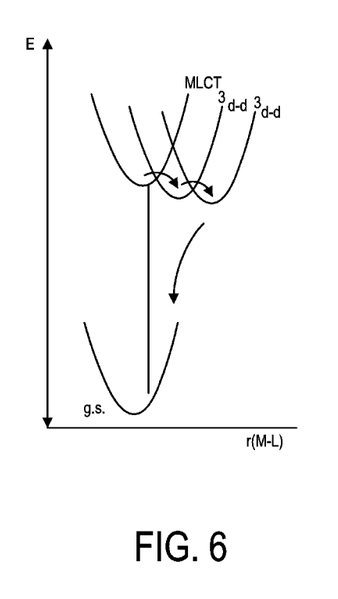
FIG. 6 is an energy state transition diagram illustrating energy state transitions of a metal complex dye having a photon emission quencher according to one example.

FIG. 6 is an energy state transition diagram illustrating properties of metal complex dyes. FIG. 6 is an energy state transition diagram for Cr $(CN^{tBu}Ar_3NC)_3$. Referring to the energy state transition diagram of FIG. 6, metal complexes can lead to ultrafast non-radiative (non-autofluorescence) relaxation due to metal centered states being below the metal-2-ligand charge-transfer (MLCT) complex. For Cr $(CN^{tBu}Ar_3NC)_3$) depicted in the energy state transition diagram in FIG. 6, the ligand field can be sufficiently weak that metal centered$^{3d\text{-}d}$ excited states can be energetically below the MLCT complex leading to ultrafast excited state. Metal complex dyes can exhibit ultrafast excited state depopulation via non-radiative relaxation. According to the energy state transition diagram of FIG. 6 a metal complex functioning as a photon emission quencher quenches photons so that a return to ground state is accompanied by phonon emission and release of thermal energy rather than photon emission.

To provide filter material, dye molecules in powder form, e.g. having photon emission quencher, and according to one example provided by a metal complex dye, can be dissolved with a solvent and added to a liquid polymer binder to form a liquid matrix having dye molecules and polymer molecules. The liquid can be deposited into a dielectric stack cavity of detector 200 and evaporated to form a filter material comprising a solid dye and polymer matrix wherein dye molecules are suspended within a matrix of polymer binder molecules.

A filter material for forming light guide 214 according to one example can include metal complex dye molecules suspended in a polymer binder matrix as set forth herein. A formed filter material including metal complex dye molecules suspended in a polymer binder matrix can exhibit spectral profile characteristics under illumination with excitation light 101 having a center wavelength of about 523 nm as set forth with reference to spectral profile 1404 as shown in the spectral profile diagram of FIG. 3. According to one example as set forth in reference to FIG. 3 providing filter material to include a dye having a photon emission quencher (as provided with use e.g. of a metal complex dye) can reduce autofluorescence emissions signals radiating from filter material at wavelengths of about 570 nm or longer to values that are about 5 percent (observing the respective autofluorescence emissions signal values of spectral profile 1304 and spectral profile 1404 at a wavelength of about 570 nm) or less of their expected values in the case filter material is provided that includes a dye without a photon emission quencher.

Providing a matrix of dye molecules with a polymer binder molecule facilitates processability with a range of semiconductor processes e.g. chemical vapor deposition (CVD), spin coating, etching, planarizing, and the like.

According to one example filter material provided by a metal complex dye matrix can have a weight ratio of between about 70:30 dye to polymer and about 90:10 dye to polymer. At concentrations above this range, the structural integrity of the matrix can become compromised and at concentrations below, filtering performance can become compromised. According to one example filter material provided by a metal complex dye matrix can have a molecule ratio of between about 1 dye molecule: 50 polymer molecules to about 1 dye molecule:150 polymer molecules. According to one example filter material provided by a polymer binder and metal complex dye matrix can have a molecule ratio of between about 1 dye molecule: 100 polymer molecules.

While higher concentrations of dye molecules improve blockage of excitation light, examples herein recognize that increased scattering can be observed at higher concentrations. Light scattering can be addressed with further processes for filtering powder dye particles prior to mixing with a polymer binder liquid.

Figure 7:
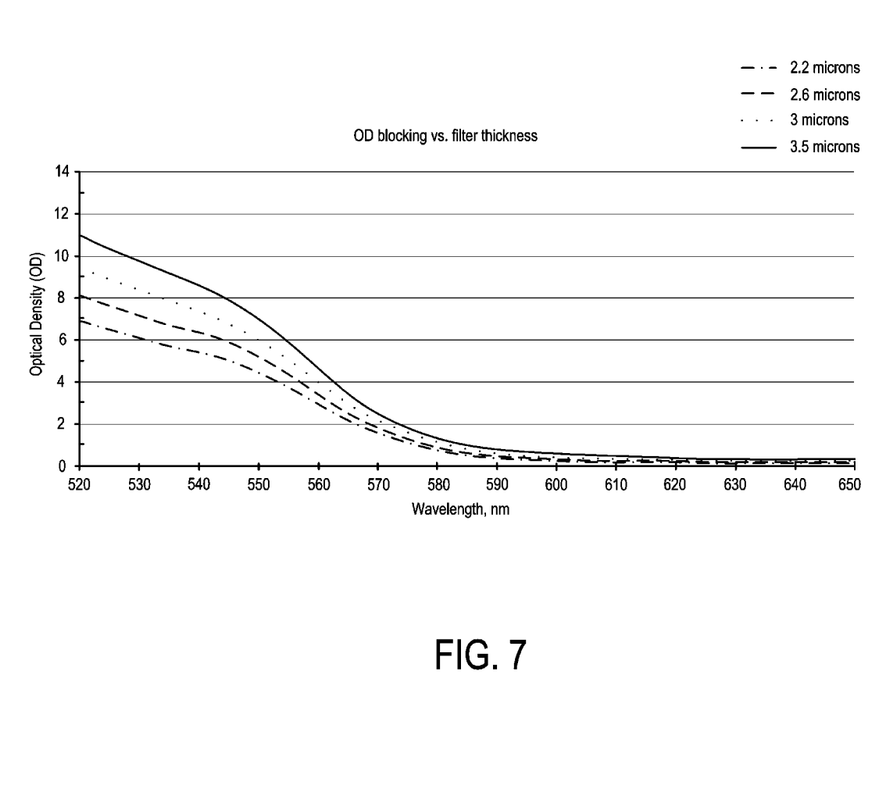
FIG. 7 depicts optical density (OD) by film thickness diagram illustrating dependence of OD on film thickness for a filter material having a metal complex dye according to one example.

FIG. 7 is an optical density (OD) film thickness diagram illustrating filtering performance of a filter material herein comprising a matrix of metal complex dye suspended in a polymer binder matrix. As seen in the OD film thickness diagram of FIG. 7, an OD of about 10 can be achieved within a spatial budget of 3.5 µm. Referring again to the spectral profile coordination diagram of FIG. 2, the spectral profile targeted for filtering is spectral profile 1202 for excitation light 101 having a center (peak) wavelength of about 523 nm. Referring to the OD film thickness diagram of FIG. 7, by configuring light guide 214 formed of a matrix of metal complex dye suspended in a polymer binder matrix to have a thickness of about 3.5 µm light guide 214 can be configured to exhibit an OD of about 10 for the center (peak) excitation light wavelength of about 523 nm. By configuring light guide 214 formed of a matrix of metal complex dye suspended in a polymer binder matrix to have a thickness of about 2 µm light guide 214 can be configured to exhibit an OD of about 7 for the center (peak) excitation wavelength of about 523 nm.

For performance of light sensing, light sensor 202 can have a particular spacing distance in reference to detector surface 206 (FIG. 1). According to one example, the particular spacing distance can be a particular spacing distance in the range, e.g. of from about 4 µm to about 6 µm. As seen in FIG. 1, light guides 214 can have space restrictions in dependence on the spacing requirements between light sensors 202 and detector surface 206. In view of the OD thickness data summarized in the OD film thickness diagram FIG. 7 material for construction of light guides 214 can be provided to satisfy targeted optical density (OD) properties in dependence on spatial properties of detector 200, and OD performance suitable for many applications is achievable even where spatial budget is restricted.

As seen by the coordination depicted by the spectral profile coordination diagram of FIG. 2, light sensors 202 can sense emissions signal light 501 attributable to fluorescence of a fluorophore but, in accordance with ideal operation, cannot detect excitation light 101 represented by spectral profile 1202. For configuring of light sensors 202 to detect emissions signal light 501 attributable to a fluorophore attached to a sample 502 without detecting excitation light 101, system 100 can include one or more filters. For example, light guides 214 can be formed of filtering material that blocks light in the energy band of excitation light 101 represented by spectral profile 1202. Thus, emissions signal light 501 represented by spectral profile 1214 is subject to detection with use of light sensors 202 without detection of excitation light 101. However, as noted, filter material forming light guide 214 can autofluoresce in response to excitation by excitation light 101. Examples herein provide light guides 214 to block excitation light 101 to exhibit reduced autofluorescence so as to preserve desired spectral profile coordination between excitation fluorescence emission and detection spectral profiles as depicted in the spectral profile coordination diagram of FIG. 2.

Examples herein recognize that left shifting of spectral profile 1220 of detector 200 can increase detection of emissions signal light 501 having a spectral profile indicated by spectral profile 1214 in the spectral profile of the emissions signal light 501. It should be understood that as used herein, left shifting refers to hypsochromic shifting, or blue shifting. Filter material herein comprising a matrix of metal complex dye suspended in a polymer binder matrix can be configured for left shifting of spectral profile 1220 by implementation of various features. In order to left shift spectral profile 1220 certain substituents of the ligands surrounding metal complex dye (2) can be altered. For instance, the phenyl groups and other moieties can act as fluorophores, and can so be altered to left shift the spectrum. For instance, methyl groups can be replaced with trifluoromethyl or other groups, and hydrogens be replaced with chlorine or bromine, in some embodiments. The spectrum can be shifted left or right, depending on the particular metal complex dye used, by replacing electron donating groups with electrons withdrawing groups and vice versa. As used herein, right shifting refers to bathochromic shifting, or red shifting, of the spectral wavelength. Thus, in any embodiment, the spectrum can be adjusted with adjustments to the functional groups of the metal complex dye.

According to one example, a filter material can include a dye having a photon emission quencher and the dye can be a non-radiant dye. According to one example, the photon emission quencher can include chromium (Cr). According to one example, the dye can be a metal complex dye having a photon emission quencher provided by a trivalent Cr transition metal ion. According to one example the filter material can be provided by matrix having a dye and polymer binder, wherein the dye has a photon emission quencher. According to one example the filter material can be provided by matrix having a dye and polymer binder, wherein the dye is a metal complex dye. According to one example the filter material can be provided by a dye suspended in a polymer matrix, wherein the dye has a photon emission quencher. According to one example the filter material can be provided by a dye suspended in a polymer matrix, wherein the dye is a metal complex dye.

Examples herein recognize that performance of system 100 can be negatively impacted by background noise, which herein refers to unwanted light energy radiating from a source external to detector 200. Examples herein recognize that a signal to noise ratio of detector 200 can be negatively impacted by fluorescence range background light radiating for sources external to detector 200. Fluorescence range noise emissions in system 100 can be attributable to sources other than autofluorescing sources within detector 200.

Examples herein recognize for example that while light energy exciter 10 can be configured to ideally emit light in a relatively shorter wavelength band, e.g. in a green wavelength band, autofluorescent sources therein, e.g. optical components can autofluoresce and light that is emitted by light energy exciter 10 can include unwanted light rays at longer wavelengths in the fluorescence band of detector 200 and light sensors 202. Examples herein recognize that fluorescence range light can enter system 100 from sources other than light energy exciter 10.

Figure 8:
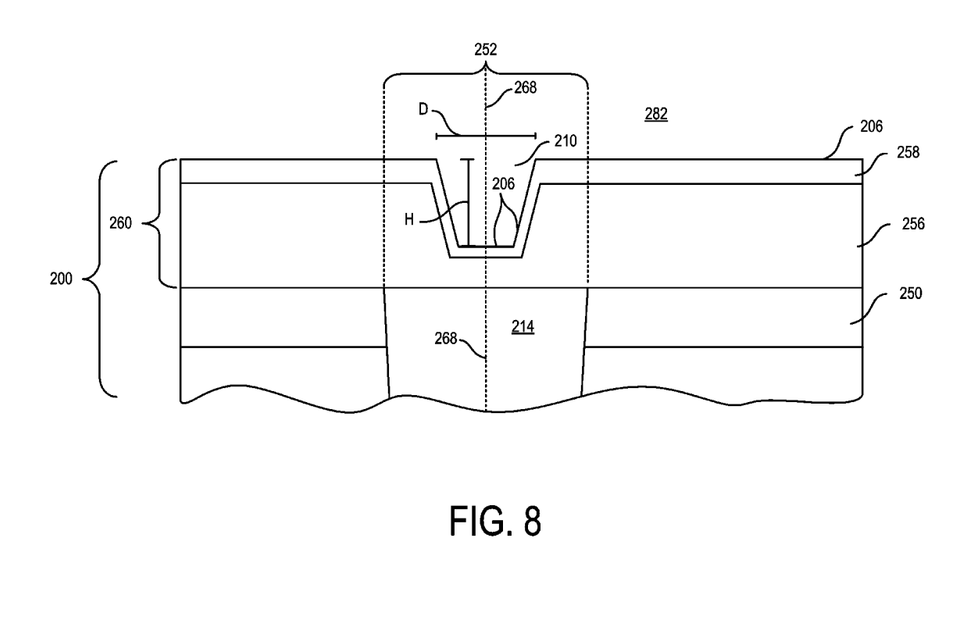
FIG. 8 is a cutaway side view of a detector having a detector surface configured to cancel incident light energy in selective wavelength bands according to one example.

In reference to FIG. 8 there are set forth additional features for increasing a signal to noise ratio of detector 200. In reference to FIG. 8 there are described features for cancellation (e.g. partial or entire cancellation) of fluorescence range background noise radiation that without the described features would be received into detector 200. Cancellation features herein can reduce fluorescence range wavelengths sensed by light sensors 202 not attributable to emissions signal light 501.

The filter material features set forth in reference to FIGS. 3-7 reduce fluorescence range noise by reduction of internal autofluorescence within detector 200. Features of detector surface 206 as set forth in connection with FIG. 8 reduce undesirable fluorescence range background noise by cancellation (e.g. partial or entire) fluorescence range light energy incident on detector surface 206. The features described with reference to FIG. 3-7 can be implemented independently of the features of FIG. 8 or according to one example in combination with the features of FIG. 8 to address the problem of fluorescence range noise with use of a combination of detector internal (FIGS. 3-7) and detector surface (FIG. 8) features.

Now referring to FIG. 8 detector 200 according to one example can be configured so that light energy incident on detector surface 206 can induce electromagnetic fields radiating from detector surface 206 that cancel (e.g. partially or entirely) incoming light energy which would otherwise be transmitted through reaction recess 210. Examples herein recognize that behavior of induced fields radiating from detector surface 206 induced from light rays incident on detector surface 206 can become more controllable and predictable as an index of refraction ratio between a detector surface 206 and fluid within flow cell 282 increases. An index of refraction of detector surface 206 can be defined by the index of refraction of the material of passivation layer 258 adjacent flow cell 282 forming the detector surface 206. Examples herein recognize that with a sufficiently high index of refraction ratio between detector surface 206 and a fluid of flow cell 282 light rays of excitation light 101 can induce electromagnetic fields radiating from detector surface 206 that cancel incoming light energy in dependence on a dimension of detector surface 206.

Referring to FIG. 8, reaction recess 210 can include a dimension "D" provided by the diameter of the reaction recess 210 at a top elevation of reaction recess 210.

Examples herein recognize that electromagnetic fields induced by incident light energy incident on reaction recess 210 can cancel incoming light energy in dependence on the dimension "D", where an index of refraction ratio between detector surface 206 and fluid within flow cell 282 is sufficiently high. Detector 200 as shown in FIG. 8 can be an integrated circuit detector having structure 260 defining detector surface 206 which can include passivation layer 256 and passivation layer 258. According to one example where passivation layer 258 having detector surface 206 is formed of tantalum pentoxide (Ta2O5) having an index of refraction $\lambda 206$ of about $\lambda 206 \approx 2.13$ and where fluid of flow cell 282 is water based and has an index of refraction $\lambda 282$ of about $\lambda 282 \approx 1.33$ the index of refraction ratio $\lambda 206/\lambda 282$ between a material forming detector surface 206 and a fluid of flow cell 282 is about $\lambda 206/\lambda 282 \approx 1.60$. According to one example where passivation layer 258 having detector surface 206 is formed of silicon nitride (SiN) having an index of refraction $\lambda 206$ of about $\lambda 206 \approx 2.02$ and where fluid of flow cell 282 is water based and has an index of refraction $\lambda 282$ of about $\lambda 282 \approx 1.33$ the index of refraction ratio $\lambda 206/\lambda 282$ between a material forming detector surface 206 and a fluid of flow cell 282 is about $\lambda 206/\lambda 282 \approx 1.52$. A three-dimensional shape of reaction recess 210 can be cylindrical or frustro-conical in some examples such that a cross-section taken along a horizontal plane that extends into the page of FIG. 8 is substantially circular. A longitudinal axis 268 can extend through a geometric center of the cross-section.

Examples herein recognize that for a detector surface 206 as set forth in FIG. 8 having a reaction recess 210 (nanowell) with the dimension D and with an index of refraction ratio $\lambda 206/\lambda 282$ suitably high there is a critical wavelength $\lambda c$ wherein wavelengths shorter than the critical wavelength $\lambda c$ are transmitted into an interior of reaction recess 210 and detector 200 and wherein wavelengths longer than the critical wavelength $\lambda c$ are cancelled (e.g. partially cancelled or entirely cancelled) by detector surface 206 having reaction recess 210. Examples herein further recognize that the described critical wavelength $\lambda c$ is in dependence of the dimension D so that the dimension D can be controlled to tune the critical dimension $\lambda c$ to a desired value. More specifically the critical wavelength $\lambda c$ can be increased by increasing the dimension D and the critical wavelength $\lambda c$ can be decreased by decreasing the dimension D. Without being bound to a particular theory in regard to the recognized effect, light rays incident on detector surface 206 may induce electromagnetic fields radiating from detector surface 206 that cancel (e.g. partially or entirely) incoming light energy which would otherwise be transmitted through reaction recess 210.

Light energy cancellation features can be advantageously incorporated into the design of detector surface 206. According to one example described with reference to FIG. 8 the dimension D can be selected to establish the critical wavelength $\lambda c$ so that wavelengths at about the center (peak) wavelength $\lambda a$ of excitation light 101 and shorter are transmitted through reaction recess 210 and into detector 200 and further so that wavelengths of about the shortest detection band wavelength $\lambda b$ and longer are cancelled by detector surface 206. Transmission of wavelengths at about the center (peak) wavelength $\lambda a$ of excitation light 101 and shorter can assure that fluorophores are properly excited according to the design of system 100 and cancellation of wavelengths of about the shortest detection band wavelength $\lambda b$ and longer can increase a signal to noise ratio of detector 200.

While $\lambda c$ can be tuned in dependence on D, the precise relationship between D and cancellation effects in dependence thereon can vary depending on materials, configuration (including light energy exciter 10 configuration), and process control parameters of a particularly fabricated system 100. Notwithstanding, information of the relationship between the dimension D and a cancellation effect in dependence thereon for a particular design of detector 200 can be determined by experimentation. On determination of information by experimentation that specifies a relationship between D and a cancellation effect for a particular design of detector 200, the information can be used to establish a value for D; that is, D=d1 where D=d1 is selected to establish the critical wavelength $\lambda c$ so that wavelengths at about a center (peak) wavelength $\lambda c$ of excitation light 101 and shorter are transmitted into reaction recess 210 and detector 200 and further so that wavelengths of about the shortest detection band wavelength $\lambda b$ and longer (i.e. in the fluorescence range) are cancelled by detector surface 206.

According to one process, one or more test sample detectors according to detector 200 can be fabricated and subject to test. The test can include testing for transmission of excitation light 101 by reaction recess 210. One or more test samples can be provided and subject to testing to determine the smallest dimension of D, D=dc at which reaction recess 210 transmits excitation light 101 in accordance with one or more transmission criterion. The one or more transmission criterion can be e.g. that a threshold amount (e.g. 90 percent, 100 percent) of maximum energy excitation light 100 is transmitted through reaction recess 210. One or more test samples can be provided and subject to testing to determine the largest dimension of D, D=de at which reaction recess 210 cancels fluorescence range light (e.g. a discernible amount of fluorescence range light) in a detection band of light sensors 102. For such testing signals read out by light sensors 202 can be examined with light guides 214 fabricated according to their production specifications. With one or more of dimensions D=dc or D=de determined, detector 200 according to a production design can be provided. In the production design according to one example, D=d1 can be provided to be in the range of from about D=dc to about D=de. In the production design according to one example, D=d1 can be provided to be at about the midpoint distance of between D=dc and D=De. In the production design according to one example, D=d1 can be provided to be about D=dc. In the production design according to one example, D=d1 can be provided to be about D=de. In the described examples, the dimension D can be provided to establish a critical wavelength $\lambda c$ so that $\lambda c$ is within a range of wavelengths of between about $\lambda a$ and about $\lambda b$, wherein wavelengths shorter than $\lambda c$ are transmitted by reaction recess 210 and wherein wavelengths longer than $\lambda c$ are cancelled by reaction recess 210, wherein $\lambda a$ is the center wavelength of excitation light 101 and wherein $\lambda b$ is the shortest detection band wavelength of the sensor array 201.

Referring to the spectral profile coordination diagram of FIG. 2, excitation light 101 can have a center (peak) wavelength of about 523 nm ($\lambda a$), and detector 200 with light sensors 202 can have a detection band commencing at about 580 nm (shortest detection band wavelength $\lambda b$). Thus, reaction recess 210 according to one example, configured to have a suitable index of refraction, can be dimensioned to permit entry of incident light energy at wavelengths of about 523 nm and shorter and can be dimensioned to cancel incident light energy at wavelengths of about 580 nm and longer. In the case where detector 200 is of a configuration wherein D≈d1 so that the distance d1 is in common with the critical wavelength λc, D can be dimensioned according to D=550 nm to transmit excitation light 101 into reaction recess 210 and to cancel unwanted fluorescence range wavelengths according to the spectral profile coordination diagram of FIG. 2. With the described configuration, the detector surface 206 can be dimensioned to permit entry of incident light energy at wavelengths of about 523 nm and shorter and can be dimensioned to cancel incident light energy at wavelengths of about 580 nm and longer.

There is set forth herein a method including subjecting a test sample detector according to detector 200 (having a structure 260 defining detector surface 206) to determine information that specifies a relationship between a dimension e.g. D of detector surface 206 and an electromagnetic field cancellation effect (e.g. including information such dc, de and/or other information relating D to λc) and wherein the fabricating the structure 260 defining a detector surface 206 includes dimensioning, using the determined information, a reaction recess 210 of the detector surface 206 to transmit excitation light 101 in an excitation wavelength band of excitation light 101 (including at the center (peak) wavelength λa) and to cancel light energy incident on the detector surface 206 in a detection band of the light sensor array 201.

A three-dimensional shape of reaction recess 210 can be cylindrical or frustro-conical in some examples such that a cross-section taken along a horizontal plane that extends into the page of FIG. 8 is circular. A longitudinal axis 268 can extend through a geometric center of the cross-section. However, other geometries can be used in alternative examples. For example, the cross-section can be square-shaped or octagonal. According to one example, shield structure 250 can have a thickness of from about 100 nm to about 600 nm, passivation layer 256 can have a thickness of from about 100 nm to about 600 nm, passivation layer 256 can have a thickness of from about 50 nm to about 500 nm, aperture 252 can have a diameter of from about 700 nm to about 1.5 μm, and reaction recess 210 if present can have a height H of from about 50 nm to about 500 nm.

Figure 9:
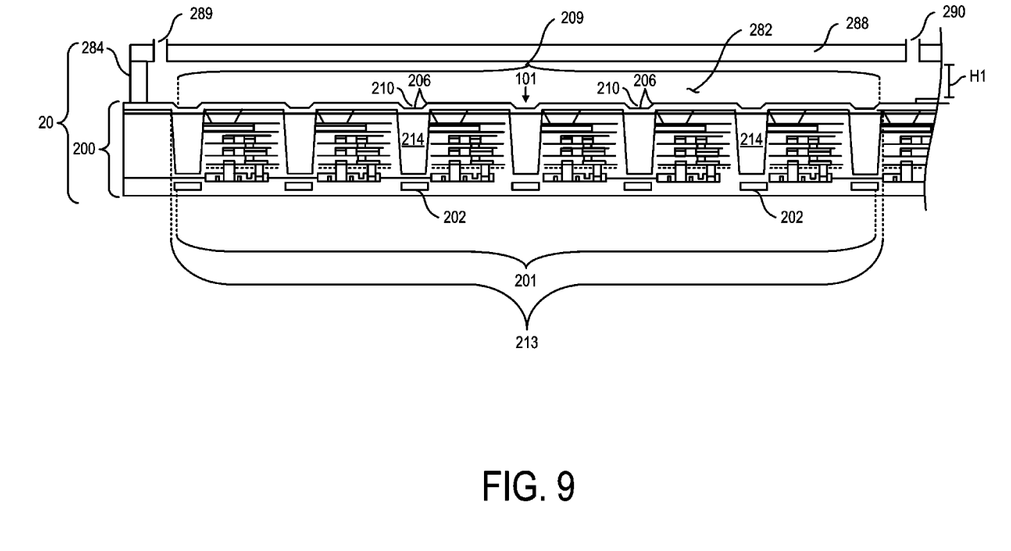
FIG. 9 is a cutaway side view of a detector having a sensor array, a light guide array and a reaction array according to one example.
Figure 10:
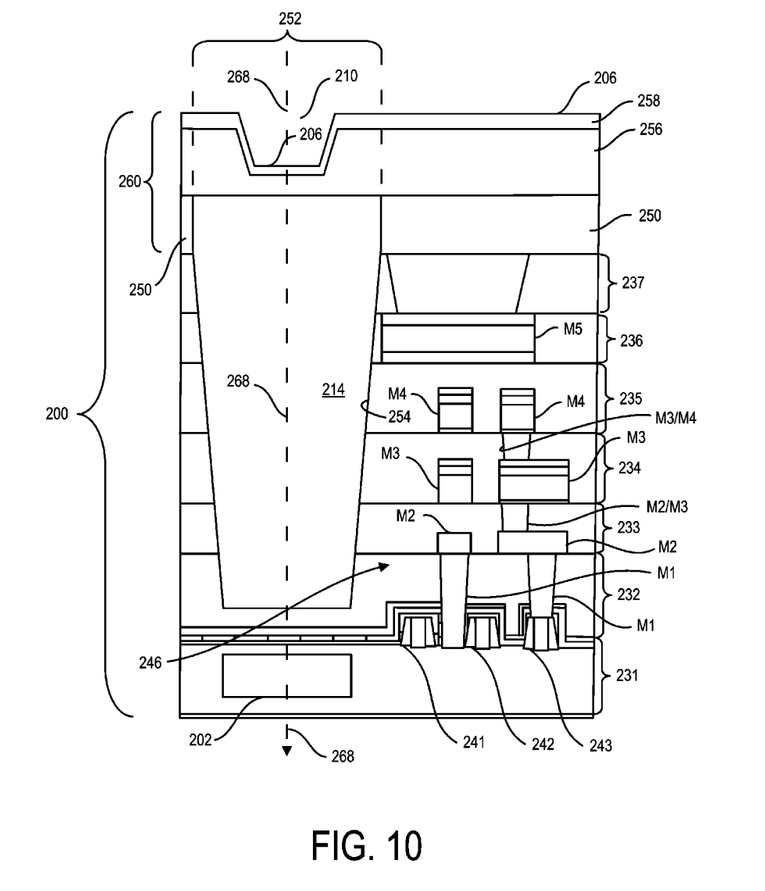
FIG. 10 is a cutaway side view of a detector having a light sensor, a light guide, and reaction recess defined by a detector surface according to one example.

FIGS. 9 and 10 illustrate further details of an example of detector 200 having one or more fluorescence range noise reducing features as set forth herein.

Referring to FIGS. 9-10 there is set forth herein a detector surface 206 for supporting biological or chemical substances; a sensor array 201 comprising light sensors 202, and circuitry 246 to transmit data signals based on photons detected by the light sensors 202; a guide array 213 comprising light guides 214; wherein light guides 214 of the guide array 213 receive excitation light 101 and emissions signal light 501 from the detector surface 206, wherein the light guides 214 extend toward respective light sensors 202 of the sensor array 201 and comprise filter material that blocks the excitation light 101 and permits emissions signal light 501 radiating from fluorescing fluorophores to propagate toward the respective light sensors 202, wherein the detector surface includes a reaction recess 210, the reaction recess comprising an index of refraction and a dimension to cancel background light energy incident on the detector surface in a detection band of the sensor array 201.

Detector 200 can include a sensor array 201 of light sensors 202, a guide array 213 of light guides 214, and a reaction array 209 of reaction recesses 210. In certain examples, the components are arranged such that each light sensor 202 aligns with a single light guide 214 and a single reaction recess 210. However, in other examples, a single light sensor 202 can receive photons through more than one light guide 214. In some examples there can be provided more than one light guide and/or reaction recess for each light sensor of a light sensor array. In some examples there can be provided more than one light guide and/or light sensors aligned to a reaction recess of a reaction recess array. The term "array" does not necessarily include each and every item of a certain type that the detector can have. For example, the sensor array of light source may not include each and every light sensor of detector 200. As another example, the guide array 213 may not include each and every light guide of detector 200. As another example, the reaction array 209 may not include each and every reaction recess 210 of detector 200. As such, unless explicitly recited otherwise, the term "array" may or may not include all such items of detector 200.

In the illustrated example, flow cell 282 is defined by sidewall 284 and a flow cover 288 that is supported by the sidewall 284 and other sidewalls (not shown). The sidewalls are coupled to the detector surface 206 and extend between the flow cover 288 and the detector surface 206. In some examples, the sidewalls are formed from a curable adhesive layer that bonds the flow cover 288 to detector 200.

The flow cell 282 can include a height H1. By way of example only, the height H1 can be between about 50-400 μm or, more particularly, about 80-200 μm. The flow cover 288 can include a material that is light transmissive to excitation light 101 propagating from an exterior of the detector assembly 20 into the flow cell 282.

Also shown, the flow cover 288 can define inlet and outlet ports 289, 290 that are configured to fluidically engage other ports (not shown). For example, the other ports can be from a cartridge (not shown) or a workstation (not shown).

Detector 200 has a detector surface 206 that can be functionalized (e.g. chemically or physically modified in a suitable manner for conducting designated reactions). For example, the detector surface 206 can be functionalized and can include a plurality of reaction sites having one or more biomolecules immobilized thereto. The detector surface 206 can have a reaction array 209 of reaction recesses 210. Each of the reaction recesses 210 can include one or more of the reaction sites. The reaction recesses 210 can be defined by, for example, an indent or change in depth along the detector surface 206. In other examples, the detector surface 206 can be planar.

FIG. 10 is an enlarged cross-section of detector 200 showing various features in greater detail. More specifically, FIG. 10 shows a single light sensor 202, a single light guide 214 for directing emissions signal light 501 toward the light sensor 202, and associated circuitry 246 for transmitting signals based on emissions signal light 501 (e.g. photons) detected by the light sensor 202. It is understood that the other light sensors 202 of the sensor array 201 (FIG. 9) and associated components can be configured in an identical or similar manner. It is also understood, however, the detector 200 is not required to be manufactured identically or uniformly throughout. Instead, one or more light sensors 202 and/or associated components can be manufactured differently or have different relationships with respect to one another.

The circuitry 246 can include interconnected conductive elements (e.g. conductors, traces, vias, interconnects, etc.) that are capable of conducting electrical current, such as the transmission of data signals that are based on detected photons. Detector 200 comprises an integrated circuit having a planar array of the light sensors 202. The circuitry 246 formed within detector 200 can be configured for at least one of read out signals from light sensors 202 after an exposure period (integration period) in which charge accumulates on light sensor 202, signal amplification, digitization, storage, and processing. The circuitry 246 can collect and analyze the detected emissions signal light 501 and generate data signals for communicating detection data to a bioassay system. The circuitry 246 can also perform additional analog and/or digital signal processing in detector 200. Light sensors 202 can be electrically coupled to circuitry 246 through gates 241-243.

Detector 200 according to one example can be provided by a solid-state integrated circuit detector such as a CMOS integrated circuit detector or a CCD integrated circuit detector. Detector 200 according to one example can be an integrated circuit chip manufactured using integrated circuit manufacturing processes such as complementary metal oxide semiconductor (CMOS) fabrication processes.

The resolution of the sensor array 201 defined by light sensors 202 can be greater than about 0.5 megapixels (Mpixels). In more specific examples, the resolution can be greater than about 5 Mpixels and, more particularly, greater than about 14 Mpixels.

Detector 200 can include a plurality of stacked layers 231-237 including a sensor layer 231, which can be a silicon layer. The stacked layers can include a plurality of dielectric layers 232-237. In the illustrated example, each of the dielectric layers 232-237 includes metallic elements (e.g. W (tungsten), Cu (copper), or Al (aluminum)) and dielectric material, e.g. SiO2. Various metallic elements and dielectric material can be used, such as those suitable for integrated circuit manufacturing. However, in other examples, one or more of the dielectric layers 232-237 can include only dielectric material, such as one or more layers of SiO2.

With respect to the specific example of FIG. 10, the dielectric layers 232-237 can include metallization layers that are labeled as layers M1-M5 in FIG. 10. As shown, the metallization layers, M1-M5, can be configured to form at least a portion of the circuitry 246.

In some examples, detector 200 includes a shield structure 250 having one or more layers that extend throughout an area above metallization layer M5. In the illustrated example, the shield structure 250 can include a material that is configured to block, reflect, and/or significantly attenuate the light signals that are propagating from the flow cell 282. The light signals can be the excitation light 101 and/or emissions signal light 501. By way of example only, the shield structure 250 can comprise tungsten (W). By way of specific example only, the excitation light 101 may have a center (peak) wavelength of about 523 nm and emissions signal light 501 can include wavelengths of about 570 nm and longer (FIG. 2).

As shown in FIG. 10, shield structure 250 can include an aperture 252 therethrough. The shield structure 250 can include an array of such apertures 252. Aperture 252 is dimensioned to allow signal emission light to propagate to light guide 214. Detector 200 can also include a passivation layer 256 that extends along the shield structure 250 and across the apertures 252. Detector 200 can also include a passivation layer 258 comprising detector surface 206 that extends along passivation layer 256 and across the apertures 252. Shield structure 250 can extend over the apertures 252 thereby directly or indirectly covering the apertures 252. Passivation layer 256 and passivation layer 258 can be configured to protect lower elevation layers and the shield structure 250 from the fluidic environment of the flow cell 282. According to one example, passivation layer 256 is formed of SiN or similar. According to one example, passivation layer 258 is formed of tantalum pentoxide (Ta2O5) or similar. Structure 260 having passivation layer 256 and passivation layer 258 can define detector surface 206 having reaction recesses 210. Structure 260 defining detector surface 206 can have any number of layers such as one to N layer.

Structure 260 can define a solid surface (i.e., the detector surface 206) that permits biomolecules or other analytes-of-interest to be immobilized thereon. For example, each of the reaction sites of a reaction recess 210 can include a cluster of biomolecules that are immobilized to the detector surface 206 of the passivation layer 258. Thus, the passivation layer 258 can be formed from a material that permits the reaction sites of reaction recesses 210 to be immobilized thereto. The passivation layer 258 can also comprise a material that is at least transparent to a desired fluorescent light. Passivation layer 258 can be physically or chemically modified to facilitate immobilizing the biomolecules and/or to facilitate detection of the emissions signal light 501.

In the illustrated example, a portion of the passivation layer 256 extends along the shield structure 250 and a portion of the passivation layer 256 extends directly along filter material defining light guide 214. The reaction recess 210 can be aligned with and formed directly over light guide 214. According to one example each of reaction recess 210 and light guide 214 can have geometric centers centered on longitudinal axis 268.

As set forth herein in connection with FIG. 8 detector surface 206 can be dimensioned so that light energy incident on detector surface 206 in a fluorescence range can be cancelled by the operation of induced electromagnetic fields. According to one example, shield structure 250 can have a thickness of from about 100 nm to about 600 nm, passivation layer 256 can have a thickness of from about 100 nm to about 600 nm, passivation layer 256 can have a thickness of from about 50 nm to about 500 nm, aperture 252 can have a diameter of from about 700 nm to about 1.5 µm, and reaction recess 210 if present can have a height of from about 50 nm to about 500 nm.

In some cases, prior to the passivation layer 256 being deposited along the shield structure 250, and prior to a depositing of shield structure 250 a cavity defined by sidewalls 254 can be formed the dielectric stack defined by dielectric layers 232-237. For example, the dielectric stack defined by dielectric layers 232-237 can be etched to form an array of the cavities defined by sidewalls 254, wherein one cavity is formed for each light sensor 202 of light sensor array 201. In particular examples, a cavity defined by sidewalls 254 is a vertically elongated space that extends from proximate the aperture 252 toward the light sensor 202.

The cavity can extend vertically along longitudinal axis 268. A three-dimensional shape of cavity defined by sidewalls 254 can be cylindrical or frustro-conical in some examples such that a cross-section taken along a horizontal plane that extends into the page of FIG. 10 is circular. The longitudinal axis 268 can extend through a geometric center of the cross-section. However, other geometries can be used in alternative examples. For example, the cross-section can be square-shaped or octagonal. According to one example the longitudinal axis 268 which is the longitudinal axis of light guide 214 can extend through a geometric center of light sensor 202 and reaction recess 210.

The filter material defining light guide 214 can be deposited within the cavity defined by sidewalls 254 after the cavity defined by sidewalls 254 is formed. For fabrication of light guide 214 according to one example, dye molecules in powder form, e.g. having photon emission quencher, can be dissolved with a solvent and added to a liquid polymer binder to form a homogeneous liquid matrix having dye molecules and polymer molecules. According to one example the dye molecules in powder form can be metal complex dye particles.

The homogeneous liquid matrix can be deposited into a dielectric stack cavity of detector 200 and evaporated to form a filter material comprising a solid dye and polymer matrix wherein dye molecules are suspended within a matrix of polymer binder molecules. The homogeneous polymer binder and dye matrix filter material can be deposited into the cavity defined by sidewalls 254, using e.g. chemical vapor deposition (CVD) physical vapor deposition (PVD). The depositing can be performed to overfill the cavity defined by sidewalls 254 with filter material and then subject to patterning such as by planarization or etching to reduce the elevation of the filter material defining light guide 214. A filter material for forming light guide 214 according to one example can include metal complex dye molecules suspended in a polymer binder molecule matrix.

The filter material can form (e.g. after curing) a light guide 214. The light guide 214 can be configured to block the excitation light 101 and permit emissions signal light 501 (FIG. 1) to propagate therethrough toward the corresponding light sensor 202. The light guide 214 can be formed of filter material described in reference to FIGS. 2-7 herein. The filter material can include a homogeneous matrix of dye and polymer binder, wherein the dye can include a photon emission quencher and according to one example is provided by a metal complex dye. The dye and polymer matrix according to one example can include a weight concentration in the range of from about 70:30 dye to polymer to about 90:10 dye to polymer. The filter material mixture can have a molecule ratio of about 1 dye molecule to about 100 polymer molecules.

The light guide 214 can be configured relative to surrounding material of the dielectric stack defined by dielectric layers 231-237 to form a light-guiding structure. For example, the light guide 214 can have a refractive index of at least about 2.0 so that light energy propagating through light guide is reflected at an interface between light guide 214 and the surrounding dielectric stack defined by dielectric layers 231-237. In certain examples, the light guide 214 is configured such that the optical density (OD) or absorbance of the excitation light 101 is at least about 4 OD. More specifically, the filter material can be selected and the light guide 214 can be dimensioned to achieve at least 4 OD. In more particular examples, the light guide 214 can be configured to achieve at least about 5 OD or at least about 6 OD. In more particular examples, the light guide 214 can be configured to achieve at least about 5 OD or at least about 6 OD. Other features of the detector 200 can be configured to reduce electrical and optical crosstalk.

It should be appreciated that all combinations of the foregoing concepts and additional concepts discussed in greater detail below (provided such concepts are not mutually inconsistent) are contemplated as being part of the subject matter disclosed herein. In particular, all combinations of claims subject matter appearing at the end of this disclosure are contemplated as being part of the subject matter disclosed herein. It should also be appreciated that terminology explicitly employed herein that also may appear in any disclosure incorporated by reference should be accorded a meaning most consistent with the particular concepts disclosed herein.

This written description uses examples to disclose the subject matter, and also to enable any person skilled in the art to practice the subject matter, including making and using any devices or systems and performing any incorporated methods. The patentable scope of the subject matter is defined by the claims, and can include other examples that occur to those skilled in the art. Such other examples are intended to be within the scope of the claims if they have structural elements that do not differ from the literal language of the claims, or if they include equivalent structural elements with insubstantial differences from the literal languages of the claims.

It is to be understood that the above description is intended to be illustrative, and not restrictive. For example, the above-described examples (and/or aspects thereof) can be used in combination with each other. In addition, many modifications can be made to adapt a particular situation or material to the teachings of the various examples without departing from their scope. While the dimensions and types of materials described herein are intended to define the parameters of the various examples, they are by no means limiting and are merely exemplary. Many other examples will be apparent to those of skill in the art upon reviewing the above description. The scope of the various examples should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Forms of term "based on" herein encompass relationships where an element is partially based on as well as relationships where an element is entirely based on. Forms of the term "defined" encompass relationships where an element is partially defined as well as relationships where an element is entirely defined. Further, the limitations of the following claims are not written in means-plus-function format and are not intended to be interpreted based on 35 U.S.C. § 112, sixth paragraph, unless and until such claim limitations expressly use the phrase "means for" followed by a statement of function void of further structure. It is to be understood that not necessarily all such objects or advantages described above can be achieved in accordance with any particular example. Thus, for example, those skilled in the art will recognize that the systems and techniques described herein can be embodied or carried out in a manner that achieves or optimizes one advantage or group of advantages as taught herein without necessarily achieving other objects or advantages as can be taught or suggested herein.

While the subject matter has been described in detail in connection with only a limited number of examples, it should be readily understood that the subject matter is not limited to such disclosed examples. Rather, the subject matter can be modified to incorporate any number of variations, alterations, substitutions or equivalent arrangements not heretofore described, but which are commensurate with the spirit and scope of the subject matter. Additionally, while various examples of the subject matter have been described, it is to be understood that aspects of the disclosure can include only some of the described examples. Also, while some examples are described as having a certain number of elements it will be understood that the subject matter can be practiced with less than or greater than the certain number of elements. Accordingly, the subject matter is not to be seen as limited by the foregoing description, but is only limited by the scope of the appended claims.

The invention claimed is:

1. A device comprising:
a detector surface configured for supporting biological or chemical samples;
a sensor array comprising light sensors and light guides; wherein the light guides receive excitation light and emissions signal light from the detector surface, wherein the light guides extend toward respective light sensors of the sensor array and comprise filter material, and wherein the filter material comprises dye having a photon emission quencher;
wherein the dye comprises metal complex dye suspended in a polymer binder matrix.

2. The device of claim 1, wherein the dye comprises a weight concentration ratio of metal complex dye to polymer binder in the range of from about 70:30 to about 90:10.

3. The device of claim 1, wherein the detector surface includes a reaction recess for supporting a sample, wherein the reaction recess comprises an index of refraction and dimension to cancel background radiation in a detection band of the sensor array.

4. The device of claim 1, wherein the dye comprises a transition metal complex dye.

5. The device of claim 1, wherein the dye comprises a transition metal and wherein the transition metal has an absorption spectral profile overlapping a fluorescence emissions spectral profile of the dye.

6. The device of claim 1, wherein the dye comprises a metal complex dye that reduces an auto-fluorescence of the filter material.

7. The device of claim 1, wherein the filter material comprises a counter ion associated to a metal complex dye.

8. The device of claim 7, wherein the counter ion comprises an alkyl amine having at least one hydrocarbon group of at least four carbon atoms.

9. A method comprising:
depositing filter material within guide cavities of a guide cavity array that are aligned with and disposed above respective light sensors of a light sensor array, wherein the filter material comprises a metal complex dye; and
fabricating a structure defining a detector surface for supporting biological or chemical samples above cavities of the guide cavity array and light sensors of the light sensor array.

10. The method of claim 9, wherein the depositing filter material comprises using chemical vapor deposition, and wherein subsequent to the depositing, the deposited filter material is subject to processing using one or more of etching and planarizing.

11. The method of claim 9, wherein the filter material comprises a homogeneous matrix of metal complex dye and polymer binder.

12. The method of claim 9, wherein the filter material comprises a matrix of metal complex dye and polymer binder and wherein a weight concentration of metal complex dye to polymer binder is in the range of from about 70:30 to about 90:10.

13. The method of claim 9, wherein the fabricating a structure defining a detector surface comprises forming a reaction recess defined in the detector surface, wherein the forming includes configuring the reaction recess so that based on an index of refraction of the detector surface and a dimensional characteristic of the reaction recess, an induced electromagnetic field radiating from the detector surface cancels background light energy incident on the detector surface in a detection wavelength band of the light sensor array.

14. The method of claim 9, wherein the method includes subjecting one or more test sample detectors to testing to determine information relating a dimension of a detector surface to an electromagnetic field cancellation effect and wherein the fabricating the structure defining a detector surface includes dimensioning, using the determined information, a reaction recess of the detector surface to cancel light energy incident on the detector surface in a detection band of the light sensor array.

15. The method of claim 9, wherein the filter material comprises a counter ion associated to the metal complex dye.

16. The method of claim 15, wherein the counter ion comprises an alkyl amine having at least one hydrocarbon group of at least four carbon atoms.

17. A method comprising:
fabricating a structure defining a detector surface for supporting biological or chemical samples above cavities of a guide cavity array and light sensors of a light sensor array, wherein the fabricating a structure defining a detector surface comprises forming a reaction recess defined in the detector surface so that based on an index of refraction and a dimensional characteristic of the reaction recess, an induced electromagnetic field radiating from the detector surface cancels background light energy incident on the detector surface in a detection wavelength band of the light sensor array.

18. The method of claim 17, wherein the reaction recess comprises an index of refraction and a dimension sufficient to transmit a center wavelength of excitation light.

19. The method of claim 17, wherein the index of refraction and the dimension characteristic if the reaction recess are sufficient to establish a critical wavelength $\lambda c$ so that $\lambda c$ is within a range of wavelengths of between about $\lambda a$ and about $\lambda b$, wherein wavelengths shorter than $\lambda c$ are transmitted by the reaction recess and wherein wavelengths longer than $\lambda c$ are cancelled by the reaction recess, wherein $\lambda a$ is the center wavelength of excitation light and wherein $\lambda b$ is the shortest detection band wavelength of the sensor array.

* * * * *